(12) United States Patent
Seshan et al.

(10) Patent No.: US 6,377,831 B1
(45) Date of Patent: Apr. 23, 2002

(54) REAL-TIME MR IMAGE SUBTRACTION AND RECONSTRUCTION

(75) Inventors: Viswanathan Seshan, Tokyo (JP); J. Andrew Derbyshire, Baltimore; Thomas K. F. Foo, Rockville, both of MD (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/449,432

(22) Filed: Nov. 24, 1999

(51) Int. Cl.$^7$ ................................................. A61B 5/05
(52) U.S. Cl. ..................... 600/407; 600/410; 600/425; 600/431; 324/307; 324/309; 378/98.12
(58) Field of Search .................................. 600/407, 410, 600/411, 425–431; 324/307, 309; 378/98.12

(56) References Cited

U.S. PATENT DOCUMENTS 4,204,225 A * 5/1980 Mistretta
5,873,825 A * 2/1999 Mistretta et al.
6,044,290 A * 3/2000 Vigen et al.

OTHER PUBLICATIONS

Winchester, P.A., Lee, H.M., Khilnani, N.M., Wang, Y., Trost, D.W., Bush, H.L., Sos, T.A., "Comparison of Two–dimensional MR Digital Subtraction Angiography of the Lower Extremity with X–Ray Angiography," JVIR 1998; 9:891–899.

Lee H.M., Wang, Y., Sostman, H.D., Schwartz, L.H., Khilnani, N.M., Trost, D.W., Ramirez de Arellano, E., Teeger, S., Bush, H.L. Jr., "Distal Lower Extremity Ateries: Evaluation with Two–Dimensional MR Digital Subtraction Angiography", *Radiology* 1998 May 207:2 505–12.

Willig, D.S., Turski, P.A., Frayne, R., Graves, V.B., Korosec, F.R., Swan, J.S., Mistretta, C.A., Grist, T.M., "Contrast–enhanced 3D MR DSA of the Carotid Artery Bifurcation: Preliminary Study of Comparison with Unenhanced 2D and 3D Time–of–Flight MR Angiography", *Radiology* 1998 Aug. 208:2 447–51.

Wang, Y., Johnston, D.L., Breen, J.F., Huston, J., Jack, C.R., Julsrud, P.R., Kiely, M.J., King, B.F., Riederer, S.L., Ehman, R.L., "Dynamic MR Digital Subtraction Angiography Using Contrast Enhancement, Fast Data Acquisition, and Complex Subtraction", MRM 1996 36:551–556.

* cited by examiner

*Primary Examiner*—Marvin M. Lateef
*Assistant Examiner*—Runa Shah Qaderi
(74) *Attorney, Agent, or Firm*—Timothy J. Ziolkowski; Michael A. Della Penna

(57) ABSTRACT

A system and method for creating MR images using mask data that is copied forward for on-the-fly image subtraction for use within such techniques as MR angiography is disclosed. The invention includes acquiring an MR mask image comprised of a plurality of k-space lines, and then copying the k-space line data of the MR mask image into a number of different memory locations. The number of different memory locations corresponds to a preselected number of MR image acquisitions as set by an MR operator. The invention next includes acquiring the preselected number of MR images, each comprised of k-space line data. As the k-space line data is acquired, it is then immediately accumulated in one of the memory locations having the MR mask image k-space line data. By setting a polarity of the data stored, each acquired k-space line of an acquired MR image is subtracted from a corresponding k-space line of the MR mask image in real time. The image is then reconstructed using the subtracted k-space line data. After each additional MR image acquisition, the data is accumulated with the masked data, which result is used for reconstructing an MR image without the need to transfer the data to another workstation for separate processing or post-processing. In this manner, the acquired data is automatically subtracted on-the-fly, thereby yielding fluoroscopic images, for example, without the prior art penalties of excessive image reconstruction time and image post-processing time.

25 Claims, 2 Drawing Sheets

REAL-TIME MR IMAGE SUBTRACTION AND RECONSTRUCTION

BACKGROUND OF THE INVENTION

The present invention relates generally to magnetic resonance imaging (MRI), and more particularly to real-time MR image processing, including a method and apparatus to perform MR image subtraction on-the-fly.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In contrast enhanced MR angiography (MRA), MR images are obtained of an artery or other blood carrying vessel in the peripheral vasculature of a patient. Data is usually acquired after an initial test bolus of contrast agent is injected into the patient and is timed as it travels along the vessel or other conduit from one station to the next. After the bolus travel time is known, an exam bolus is injected and MR data is acquired at each scan station where the bolus is located.

Phase contrast MRA is another practical and clinically applicable technique for imaging blood flow. MRA makes use of flow encoding gradient pulses which impart a velocity-dependent phase shift to the transverse magnetization of moving spins while leaving stationary spins unaffected. Each phase contrast acquisition generates two images: a magnitude image that is proportional to the proton density of the object and may also be $T_1$-weighted, and an image representing the phase of the object. The phase image produced has information only from the moving spins and the surrounding stationary tissue is suppressed. Images representing both the average flow over the entire cardiac cycle and at a series of individual points in the cycle have been generated using this technique. The phase contrast MR method produces phase images with intensities that represent the magnitude of the flow velocity and also the direction of flow. Therefore, such images may be used for both qualitative observation of blood flow and quantitative measurement. The practical application of phase contrast MR angiography and venography to the quantitative determination of flow velocity is therefore evident.

The most common approach to MRA involves collecting a mask image first, then collecting a series of images subsequent, and then subtracting the mask image from each of the images in the series after image reconstruction. For near real-time applications, all of the images are transferred to a separate workstation where a subtraction is performed, and the subtracted images are transferred back to the operator's console for display.

In these "near real-time" subtraction angiography techniques, which are typically done on a second workstation, a reference or baseline image is first collected, which is then transferred to the second workstation and stored, either as a positive or a negative image. Data is then collected during subsequent passes and each is individually transferred to the second workstation. Thereafter, after all the data is collected, a subtraction of the images is performed offline. Once the data is subtracted, the image can be displayed either on the second workstation or sent back to the operator's console, as desired.

It would therefore be desirable to have a method and apparatus for real-time data subtraction during acquisition with minimal computation time such that images can be reconstructed on-the-fly and displayed on an operator's console.

SUMMARY OF THE INVENTION

The present invention relates to a system and method of real-time image processing including MR image subtraction and reconstruction that overcomes the aforementioned problems.

The invention includes an MR digital processing technique wherein a mask image is copied forward multiple times in acquisition memory. Subsequently acquired data is automatically subtracted on-the-fly, thereby yielding images without the typical prior art penalties involved in image reconstruction and image post-processing time.

In accordance with one aspect of the invention, a method of real-time MR image processing includes acquiring an MR mask image comprised of k-space line data and copying the k-space line data of the MR mask image into a number of different memory locations, the number of which corresponds to a preselected number of MR image acquisitions, as set by an MR operator. The method next includes acquiring the preselected number of MR images and accumulating the k-space line data of each acquired MR image in a corresponding memory location with the k-space line data of the MR mask image. By setting a polarity of the stored data, or the newly acquired data, the present invention provides a method for real-time subtraction during acquisition without post-processing or the use of a separate processing station. Computation time is minimal due to the subtraction occurring in-place as each line of k-space is acquired, and therefore, the subtracted images are reconstructed on-the-fly. Either positive or negative reverse contrast images, are easily obtainable by simply setting a flag to set the polarity of the mask data that is copied forward into memory.

In accordance with another aspect of the invention, an MRI apparatus to process MR images in real-time is disclosed in which a magnetic resonance imaging system having a plurality of gradient coils positioned about a bore of a magnet to impress a polarizing magnetic field has an RF transceiver system and an RF switch controlled by a pulse module to transmit RF signals to an RF coil assembly to acquire MR images, and a computer programmed to acquire the MR mask image data and copy the acquired MR mask image data into a number of different memory locations. The computer is then programmed to acquire a predetermined number of MR image data sets and then accumulate the acquired MR image data sets in the same memory locations as the acquired MR mask image data.

In accordance with yet another aspect of the invention, a computer memory medium is disclosed having thereon a computer program for use with an MRI apparatus which, when executed, causes a computer to acquire MR mask image data and copy that acquired MR mask image data into a number of different memory locations. The computer is also programmed to acquire MR image data for a number of image acquisitions as set by an operator and then accumulate the acquired MR image data into the same memory locations as the acquired MR mask image data previously saved.

The present invention is particularly useful in MR angiography where digital subtraction of MR images has heretofore been time consuming and memory intensive. Use of the present invention in MR angiography provides a fast digital subtraction of a mask image and subsequently acquired data automatically and on-the-fly, thereby yielding fluoroscopic images without the typical penalties in image reconstruction or image post-processing time.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
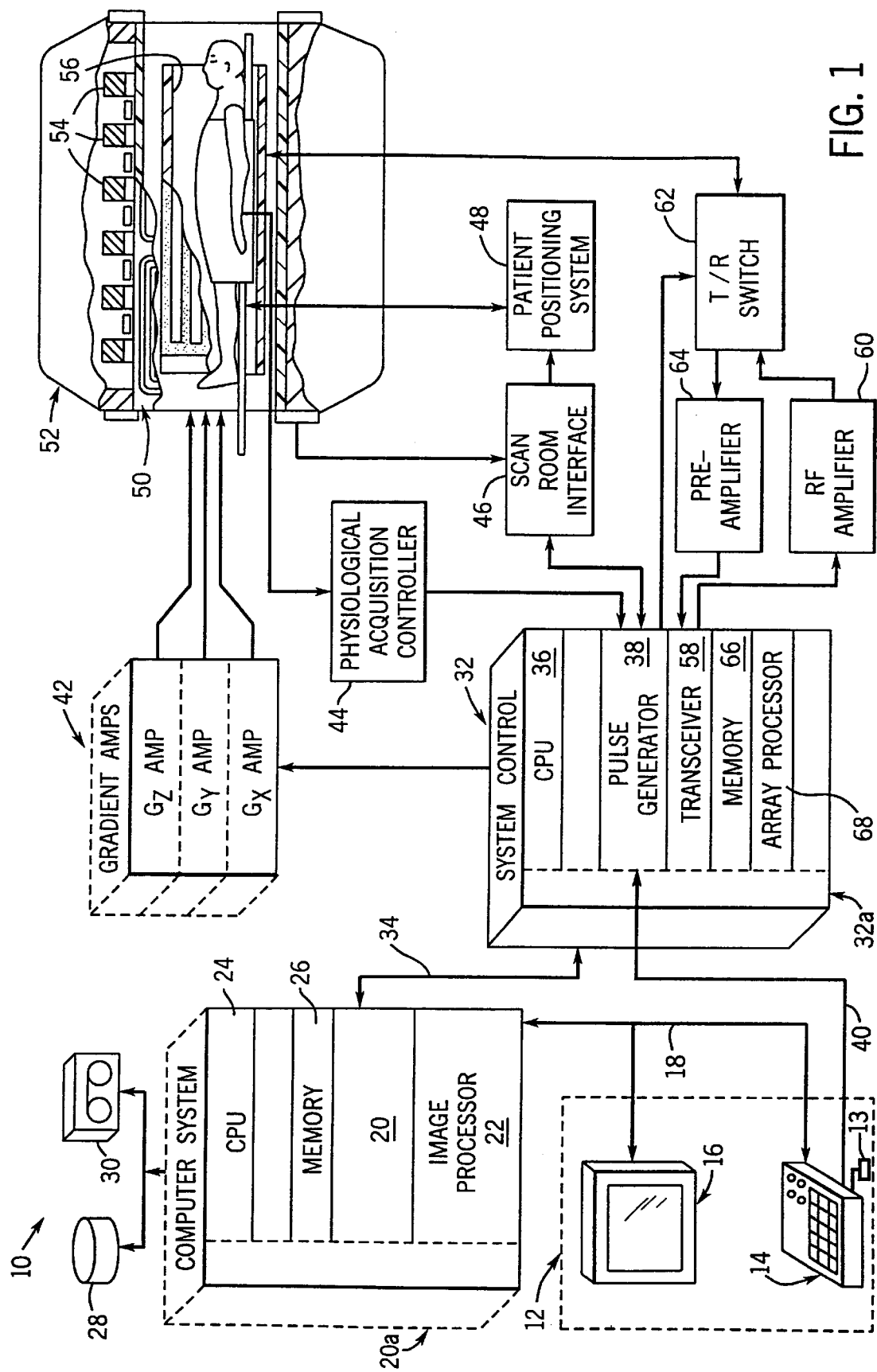
FIG. 1 is a schematic block diagram of an NMR imaging system for use with the present invention.

Referring to FIG. 1, the major components of a preferred MRI system 10 incorporating the present invention are shown. The operation of the system is controlled from an operator console or interface 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28 and a tape drive 30 for storage of image data and programs, and it communicates with a separate system control 32 through a high speed serial link 34. The input device 13 can include a mouse, joystick, keyboard, track ball, touch screen, light wand, voice control, or similar such device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 also receives patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding gradient coil in an assembly generally designated 50 to produce the magnetic field gradients used for position encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals radiated by the excited nuclei in the patient may be sensed by the same RF coil 56 and coupled through the transmit/receive switch 62 to a preamplifier 64. The amplified NMR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

In order to appreciate the present invention, it is significant to understand how data is handled in prior art systems. The following is a brief description of the acquisition and storage of MR data. The NMR signals picked up by the RF coil 56 are digitized by the transceiver module 58 and transferred to a memory module 66 in the system control 32. When a scan is completed, an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

The present invention includes a method and system suitable for use with the above-referenced NMR system, or any similar or equivalent system for obtaining MR images without having to read and write to memory multiple times in a separate workstation and without subsequent image post-processing time.

Figure 2:
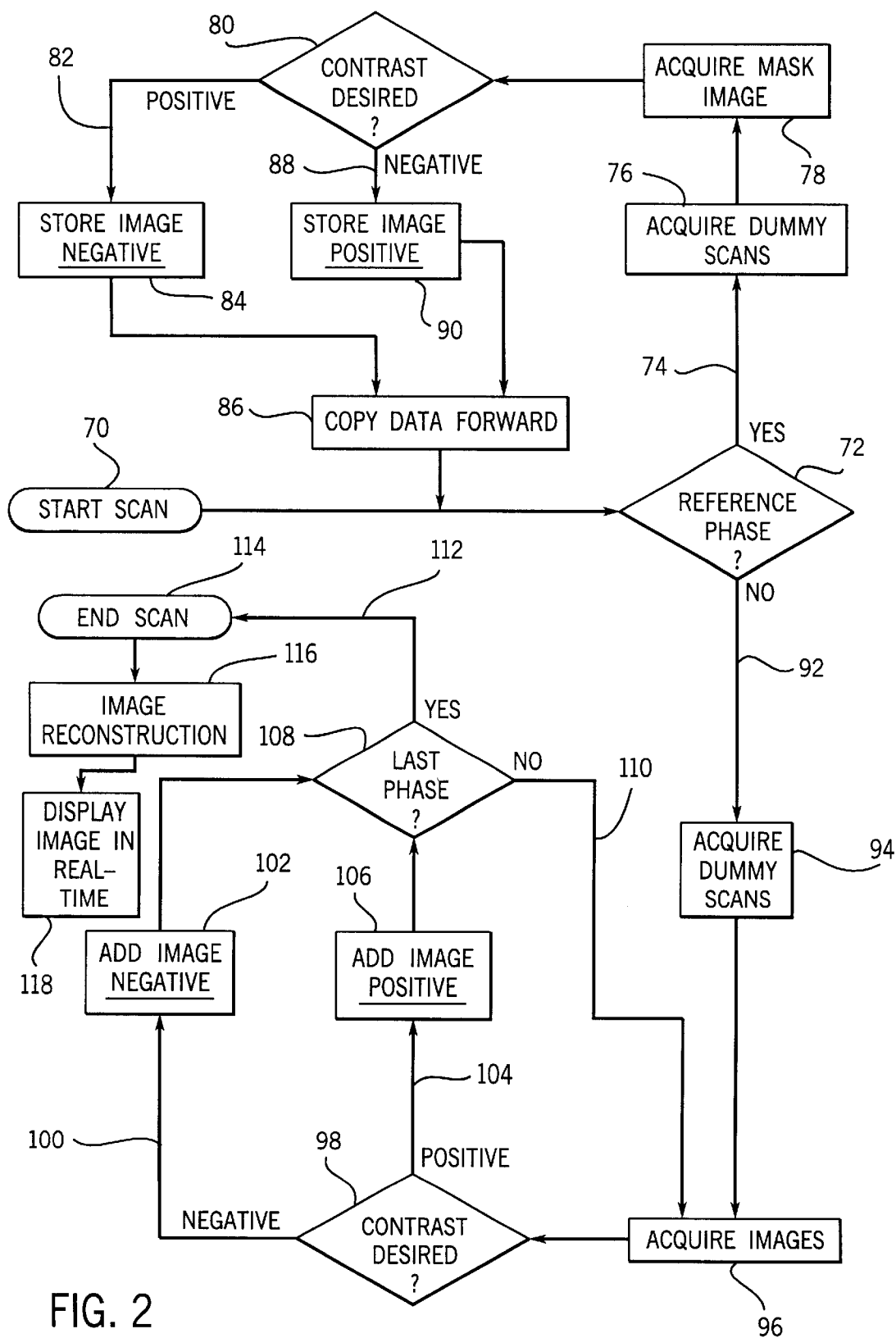
FIG. 2 is a flowchart of the present invention for use with the system of FIG. 1.

Referring to FIG. 2, when a scan is first initialized 70, the system is programmed to check to see if a mask image has been acquired in a reference phase 72. On initialization, a reference phase flag is set so as to acquire a mask image 74. However, the system must first run through a number of dummy scans 76 in order to obtain equilibrium and then acquire an MR mask image is acquired at 78. Thereafter, based on an operator input to the interface 12 and 13, FIG. 1, a decision is made as to whether or not contrast is desired at 80, FIG. 2. If a positive contrast is desired 82, the image is stored with a negative polarity 84 and the data is copied forward into bulk access memory at 86. If a negative contrast is sought 80, 88 the image is stored with a positive polarity 90 and the data is then copied forward at 86.

In copying the data forward at 86, the computer is programmed to copy each k-space line data of the MR mask image into a number of different memory locations in the on-board RAM. The number of different memory locations is the same as a preselected number of image acquisitions set by an MR operator prior to the start of the scan 70. In other words, the same set of data for the mask image is copied multiple times "forward" in acquisition memory. By example, if the operator specifies that five multi-phase MR images are to be acquired, once the mask image data is acquired at 78, and the contrast is set, five sets of identical mask image data, with appropriate contrast polarity, is copied into five different memory locations.

Once the reference phase is complete 72, 92 the equilibrium state should again be achieved by first acquiring a number of dummy scans 94. Once equilibrium is reached, the appropriate number of MR images are acquired at 96, as set by the operator. If a negative contrast is sought 98, 100, then the image data is added with a negative polarity to one of the aforementioned memory locations at 102. If a positive contrast is sought 98, 104, then the acquired image data is added with a positive polarity to one of the aforementioned memory locations having the stored masked data at 106. It is noted and understood that in the functional blocks 102 and 106, the data is being accumulated into the same memory location as the aforementioned masked data as stored in functional blocks 84 and 90. In this manner, with the appropriate setting of the data polarities, by accumulating the data in the same memory locations, the data is effectively added or subtracted, based on the contrast sought. Until the last phase has been acquired 108, 110, a next image is acquired at 96, and depending on contrast desired 98, is accumulated appropriately at 102 and 106. In the aforementioned example, five MR images would be acquired at step 96. Once the last phase is complete 108, 112 the MR scan acquisition is complete at 114, at which time the image reconstruction is immediately performed 116 and the image is displayed in real-time 118 on the display 16, FIG. 1.

Accordingly, the invention includes a method of real-time MR image processing having the steps of first acquiring an MR mask image having a plurality of k-space line data, and then copying the k-space line data of the MR mask image into a number of different memory locations. The number of different memory locations corresponds to the preselected number of MR image acquisitions set by an MR operator. The preselected number of MR images, each having a plurality of k-space line data, are then acquired, and that data is accumulated in one of the corresponding memory locations. That is, one of the memory locations in which the k-space line data of the MR mask image was previously stored.

The method further includes setting a polarity of the k-space line data to reconstruct an image of desired contrast as determined by an MR operator. The step of copying k-space line data is further defined as copying the same k-space line data in bulk to multiple locations in memory for real-time processing on-the-fly.

The pulse sequence is set up such that the user can sequentially collect the k-space line data in a single pass scan or interleave k-space line data collection, thereby collecting each phase in alternating scan passes. In the latter case, the number of phases also determines the number of passes in the scan. The main disadvantage to collecting all the phases in a single pass is that reconstruction times can be undesirably long. For real-time applications, the interleaved acquisition is preferred. The data collected from each subsequent phase is subtracted on-the-fly from the copy of the mask image data stored at the appropriate memory location. The method includes reconstructing an MR image using the accumulated k-space line data from each memory location used to store the k-space line data of the MR mask image, and displaying the reconstructed MR image at an operator console without using another workstation for post-processing. As previously mentioned, depending on the contrast desired, the step of accumulating can include a data subtraction or a data addition depending on the polarity of the data as set by the contrast desired.

The invention also includes an MRI apparatus to subtract MR images in real-time that includes an MRI system having a plurality of gradient coils positioned about a bore of a magnet to impress a polarizing magnetic field and an RF transceiver system, including an RF modulator controlled by a pulse control module to transmit RF signals to an RF coil assembly in order to acquire MR images. The MRI apparatus includes a computer programmed to acquire MR mask image data and copy that acquired MR image data to a number of different memory locations. Once the MR mask image data is stored in a number of different memory locations, the computer is programmed to acquire the MR image data and accumulate that acquired MR image data in the same memory locations as the acquired MR mask image data for real-time image subtraction and reconstruction. The apparatus includes an operator interface 12 connected to the computer 24 to select a desired number of MR image acquisitions. The number of memory locations in memory 26 that computer 24 copies the acquired MR mask image data to, is the same as the desired number of MR image acquisitions set by an operator as input to interface 12. The operator interface 12 also allows an operator to input a desired image contrast and the computer sets a polarity of either the mask image data or the MR image data so that when the data is accumulated in memory, either an automatic subtraction or addition is performed to obtain the desired image contrast. The computer is also programmed to reconstruct and display a subtracted MR image on display 16 in real-time by subtracting data as each line of k-space data is acquired. Memory 26 of computer 24 comprises bulk access memory capable of receiving complex k-space line data in bulk and accumulating the received data with newly acquired data. The computer is programmed to transmit a pulse sequence so that a user can choose to collect data for all the passes in a single pass or in separate passes.

The invention also includes a computer readable storage medium such as disk storage 28, tape drive 30, or any other data storage medium, such as a floppy disk, having thereon a computer program comprising instructions for use with an MRI apparatus which, when executed by a computer, cause the computer to acquire MR mask image data, copy the acquired MR mask image data to a number of different memory locations, acquire MR image data for a pre-specified number of phases, and accumulate the acquired MR image data from each phase in the same memory locations as the acquired MR mask image data for on-the-fly, real-time MR image processing. The computer program further causes the computer to receive an external data request indicating a desired number of MR image acquisitions and to set the number of memory locations in which MR mask image data is copied to, to the same number of desired MR image acquisitions. The computer is also programmed to receive an external data request indicating a desired MR image contrast and to set a polarity of the MR mask image data to reconstruct an MR image according to the desired MR image contrast. The computer is also programmed to reconstruct and display the MR image of a desired contrast in real-time so as to avoid post-processing and the use of a second computer for processing. That is, each line of k-space data acquired is subtracted from the MR mask image data in real-time. The computer includes bulk access memory designed to receive large amounts of data in blocks and accumulate after-acquired data with presently-stored data in the same memory locations. The computer is programmed to either sequentially collect k-space line data in a single phase of a multi-phase acquisition or interleave k-space line data acquisitions in alternate phases of a multi-phase acquisition.

Although the present invention is readily applicable to MR angiography, it is readily apparent to those skilled in the art, that the present invention is applicable to any image processing in which subsequent acquired images are added or subtracted to a mask image.

The present invention has been described in terms of the preferred embodiment, and it is recognized that equivalents, alternatives, and modifications, aside from those expressly stated, are possible and within the scope of the appending claims.

We claim:

1. A method of real-time image processing comprising the steps of:
    acquiring a mask image comprised of k-space line data;
    copying the k-space line data of the mask image to a number of different memory locations, the number of different memory locations corresponding to a preselected number of image acquisitions;
    acquiring the preselected number of images, each comprised of k-space line data; and
    accumulating the k-space line data for each acquired image with the k-space line data of the mask image in a corresponding memory location.

2. The method of claim 1 wherein the step of copying the k-space line data of the mask image further includes setting a polarity of the k-space line data to reconstruct an image of desired contrast.

3. The method of claim 1 wherein the step of copying k-space line data is further defined as copying identical k-space line data in bulk to multiple memory locations for real-time processing.

4. The method of claim 1 further comprising the step of sequentially collecting k-space line data in a single pass scan.

5. The method of claim 1 further comprising the step of interleaving k-space line data collection, thereby collecting each phase in alternating scan passes.

6. The method of claim 1 further comprising the step of reconstructing an image using the accumulated k-space line data from each memory location used to store the k-space line data of the mask image.

7. The method of claim 6 further comprising displaying the reconstructed image at an operator console without using another workstation for postprocessing.

8. The method of claim 1 wherein each step is performed in real-time at an operator console without transfer of data to another workstation.

9. The method of claim 1 wherein the step of accumulating includes adding data pre-existing in the memory location with newly acquired k-space line data.

10. An MRI apparatus to process MR images in real-time comprising:
    a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and
    a computer programmed to:
        acquire MR mask image data;
        copy the acquired MR mask image data to a number of memory locations;
        acquire MR image data; and
        accumulate the acquired MR image data in the same memory locations as the acquired MR mask image data.

11. The MRI apparatus of claim 10 further comprising an operator interface connected to the computer to select a desired number of MR image acquisitions, and wherein the number of memory locations is the same as the desired number of MR image acquisitions.

12. The MRI apparatus of claim 10 further comprising an operator interface connected to the computer to select a desired image contrast and wherein the computer sets a polarity of one of the MR mask image data and the MR image data so that the accumulate act performs an appropriate mathematical operation to obtain the desired image contrast.

13. The MRI apparatus of claim 10 further comprising an operator interface connected to the computer to select a desired image contrast and wherein the act of copying the acquired MR mask image data also includes setting a polarity opposite that of subsequent acquired MR image data such that the accumulation act performs real-time MR image complex subtraction.

14. The MRI apparatus of claim 10 wherein the computer is further programmed to reconstruct and display a subtracted MR image on a display in real-time by subtracting data as each line of k-space data is acquired.

15. The MRI apparatus of claim 10 wherein the computer comprises bulk access memory capable of receiving complex k-space line data in bulk and accumulating received data with newly acquired data.

16. The MRI apparatus of claim 10 wherein the computer is further defined to sequentially collect k-space line data in a single pass scan.

17. The MRI apparatus of claim 10 wherein the computer is further defined to interleave k-space line data acquisition, to thereby collect each phase in alternating scan passes.

18. A computer readable storage medium having stored thereon a computer program for use with an imaging apparatus comprising instructions which, when executed by a computer, cause the computer to:
    acquire mask image data;
    copy the acquired mask image data to a number of memory locations;
    acquire image data; and
    accumulate the acquired image data in the same memory locations as the acquired mask image data.

19. The computer readable storage medium of claim 18 wherein the computer program further causes the computer to receive an external data request indicating a desired number of image acquisitions and to set the number of memory locations in which mask image data is copied to, to the number of desired image acquisitions.

20. The computer readable storage medium of claim 18 wherein the computer program further causes the computer to receive an external data request indicating a desired image contrast and set a polarity of the mask image data to reconstruct an image according to the desired image contrast.

21. The computer readable storage medium of claim 18 wherein the computer program causes a computer to reconstruct and display an image of desired contrast in real-time.

22. The computer readable storage medium of claim 18 wherein the computer program further cause the computer to subtract each line of k-space data acquired from the mask image data in real-time without use of a second computer and without post-processing.

23. The computer readable storage medium of claim 18 wherein the computer comprises bulk access memory designed to receive large amounts of data in blocks and accumulating after-acquired data with presently stored data.

24. The computer readable storage medium of claim 18 wherein the computer program further causes the computer to sequentially collect k-space line data in a single pass of a multi-phase acquisition.

25. The computer readable storage medium of claim 18 wherein the computer program further causes the computer to interleave k-space line data acquisition in alternate phases of a multi-phase acquisition.

* * * * *